(12) United States Patent
Fouillet et al.

(10) Patent No.: US 7,094,379 B2
(45) Date of Patent: Aug. 22, 2006

(54) DEVICE FOR PARALLEL AND SYNCHRONOUS INJECTION FOR SEQUENTIAL INJECTION OF DIFFERENT REAGENTS

(75) Inventors: Yves Fouillet, Voreppe (FR); Nicolas Sarrut, Seyssinet (FR); Antoine Gruss, Seyssinet (FR)

(73) Assignee: Commissariat a l'Energie Atomique, Paris (FR)

( * ) Notice: Subject to any disclaimer, the term of this patent is extended or adjusted under 35 U.S.C. 154(b) by 483 days.

(21) Appl. No.: 10/277,754

(22) Filed: Oct. 23, 2002

(65) Prior Publication Data

US 2003/0082081 A1 May 1, 2003

Related U.S. Application Data

(60) Provisional application No. 60/362,440, filed on Mar. 8, 2002.

(30) Foreign Application Priority Data

Oct. 24, 2001 (FR) .................................. 01 13734

(51) Int. Cl.
*B01L 3/00* (2006.01)
(52) U.S. Cl. .......................................... 422/100; 137/13
(58) Field of Classification Search ................ 422/100, 422/102, 81, 82; 137/13, 828
See application file for complete search history.

(56) References Cited

U.S. PATENT DOCUMENTS 3,424,557 A 1/1969 Skeggs

| 5,101,848 A | 4/1992 | Kojima et al. |
| 5,942,443 A * | 8/1999 | Parce et al. ................. 436/514 |
| 2001/0041357 A1 | 11/2001 | Fouillet et al. |

FOREIGN PATENT DOCUMENTS

| FR | 1 490 015 | 7/1967 |
| FR | 1 540 191 | 9/1968 |
| GB | 1186197 | 9/1967 |
| WO | WO 01/07159 | 2/2001 |

* cited by examiner

*Primary Examiner*—Jill Warden
*Assistant Examiner*—Natalia Levkovich
(74) *Attorney, Agent, or Firm*—Oblon, Spivak, McClelland, Maier & Neustadt, P.C.

(57) ABSTRACT

The invention relates to a microfluidic device for injecting series of mobile reaction chambers (102, 103) having non-miscible segmenters (101) in micro-channels (21 to 26), comprising:
  injection means (10) for injecting into microreaction channels alternatingly and in parallel liquid to form mobile reaction chambers and liquid for forming the segmenters;
  means for controlling the progression of one of the two liquids, applied to act on one zone (31) of each microchannel delimiting an injection volume of said liquid; the control means being able to cause stopping or slowing of the progression of said liquid over the zone of each microchannel by exerting an action based on a physico-chemical property of the liquid and said action not affecting the other liquid.

20 Claims, 9 Drawing Sheets

Background Art
Fig. 1
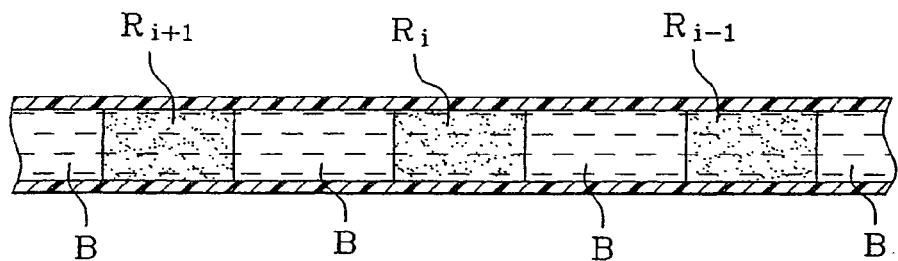
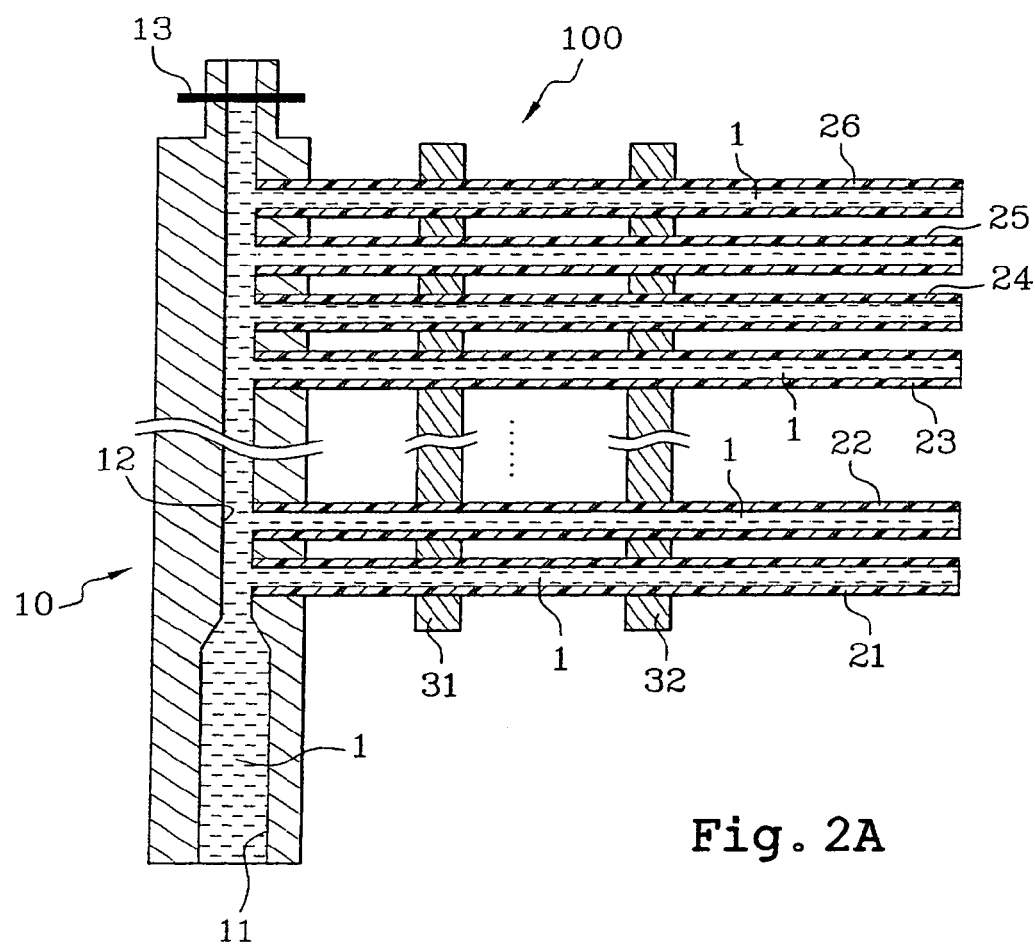
Fig. 2A

DEVICE FOR PARALLEL AND SYNCHRONOUS INJECTION FOR SEQUENTIAL INJECTION OF DIFFERENT REAGENTS

TECHNICAL FIELD

The invention relates to a device for parallel and synchronous injection for sequentially injecting different reagents. It also relates to a biological reactor and a method for implementing a biological, biochemical or chemical procedure using the samples.

In a general fashion, the invention is applicable to all filed requiring high through-put or HTS chemical or biological analysis (i.e., "high through-put screening").

DESCRIPTION OF THE PRIOR ART

One of the principles taken from microfluidic technology for biological or chemical applications is the possibility of miniaturizing, parallelizing and serializing reactions. This is, for example, very important for genomic assays requiring automated apparatuses enabling study of a large number of genes while using minimal volumes and assay time. The same applies to proteomic assays.

Miniaturization was made possible by developments in silicon, glass, or plastic microtechnologies. There is an extensive literature describing realizations of microchannels having submicronic dimensions of several tens of microns on silicon, glass or plastic.

Miniaturization allows integration of a large number of parallel channels on a very small surface. As a result, it is possible to integrate several channels operating simultaneously. This subject matter is discussed in the article, "DNA analysis with capillary array electrophoresis microplates" by R. A. MATHIES et al., appearing in *Micro Total Analysis Systems '98*.

Said realization involves circulating in at least one channel a plurality of different reactions. One therefore speaks of continuous flow or FLA (i.e., "flow injection analysis"). FIG. 1 schematically represents a series of reactions allowing circulation of several different reaction volumes. In microchannel 1, the reactions $R_{i-i}$, $R_i$, $R_{i+i}$ are circulating in the direction indicated by the arrow. It may be necessary to place segmenters in order to differentiate between two successive reactions in order to prevent or to limit mixing and contamination between reactions. We then speak of mobile reaction chambers $R_{i-i}$, $R_i$, $R_{i+i}$ and of isolator or segmenting beads. If the reaction and segmenting liquids are miscible, it must be assured that there is no diffusion between different successive reactions (see document WO-A-00/42212).

It is also possible to use segmenting beads formed by a non-miscible liquid using reaction volumes. This is then referred to as a "series of mobile reaction chambers with non-miscible segmenting" or shortened to "reaction series." It is possible to use an aqueous solution for the reactions (the most current one for biology) and oil (mineral, silicon, etc.) or an organic solvent that is non-miscible in water (octane, for example) as the segmenting beads.

One of the technical problems in realizing micro-systems based on the principle of FIA concerns the large number of micro-channels and the design of the automated apparatuses enabling production of the reaction series. In effect, the reaction series must be injected and circulated in a precise and controlled fashion within the micro-channels.

The document WO-A-01/12327 discloses a method for producing and mobilizing, in a main micro-channel, a series of reactant volumes isolated from each other by segmenting volumes. Mobilizing the liquids is achieved electrokinetically using a plurality of electrodes placed along the main micro-channel. The electrokinetic effect acts only on the mobile reaction chambers and not on the segmenting beads. This allows control at the position of the reactant volumes.

The notion of selective action on one phase of a system using two phases is already well-known in another field. For example, for petroleum applications there are automatic gates or valves which are opened when gases are circulating and which automatically closes when petroleum reaches the valve. The principle consists of using a cooling system enabling temperatures to be reached that are sufficiently low in the portion of the channel to congeal the petroleum which then blocks the channel. When it is gas that is present, it can circulate freely. Reference can be made to the U.S. Pat. Nos. 4,203,472, 4,269,212, 5,101, 848 and to the international application No. WO A 94/29690 regarding this subject matter.

WO-A-00/30751 discloses a method for transferring small volumes of liquid from a reservoir of the well-plate type to a micro-system. The transfer system is realized using a plurality of small tubes. Injection is accomplished by a pressure difference between the two ends of the tubes. The notion of congealing one of the liquids for controlling an injection volume is also disclosed. The disclosures from this document does not apply to the notion of reaction series.

It is quite possible, using the tools of the prior art, to realize on one line and using volumes of several µl, a reaction series. It is sufficient, for example, to use a system of valves and pumps. It is also possible to create and store a reaction series in a tube. It is further also possible to use a pressure system or a plunger syringe to aspirate successively the different reactants previously deposited in the wells or on a well plate.

The prior-art techniques, however, do not enable obtaining the same result using reaction volumes that are very small (less than a µl) and over a plurality of parallel channels with the same reactant having to be injected simultaneously over all of the channels. In this case, the small size of the channels induces a capillary force which are preponderant with respect to the viscosity forces. The capillary effects are very broadly random because they depend on wetting, the interface tensions between the two fluids, temperature and the surface characteristics of the sides of the channels. Thus, in practice, it is very difficult to control synchronization of parallel series.

SUMMARY OF THE INVENTION

The invention provides a solution to the problems inhering in the prior art.

The object of the invention is to provide a microfluidic device for parallel and synchronously injecting series of mobile reaction chambers with non-miscible segmenters in micro-channels, comprising:

injection means for alternatingly and in parallel injecting a liquid for forming mobile reaction chambers and liquid for forming segmenters into the micro-channels;

first controlling means for controlling the progression of one of the two liquids in the micro-channels, disposed so as to act on a zone of each micro-channel delimiting an injection volume of said liquid in each micro-channel, the first controlling means being able to cause, when it is used, the stopping or slowing of the progression of said liquid over said zone of each microchannel by effecting an action based on a physico-chemical property of said liquid, said action not directly affecting the other liquid.

These first controlling means can be means enabling arrangement of said zone of intervention of each micro-channel so as to modify the volume to be injected of said liquid between the two liquids.

Preferably, the injection means comprises a part having an injection channel communicating wit the first ends of the micro-channels. Advantageously, the injection channel at one of its ends communicates with a channel input, through which the liquids are injected; the other of its ends being equipped with means of evacuating the liquids present in the injection channel. The evacuation means can comprise a valve. The injection channel and said zone of each micro-channel can be arranged in parallel fashion, the micro-channels being perpendicular to them.

The first controlling means can be selected from among means operating thermally, means operating on a viscosity basis for slowing, means operating on the basis of magnetic effect, means operating on the basis of electrowetting and means operating by constriction of the tubes. The first controlling means operating thermally, the controlling means being chosen from the Peltier effect devices and thermal transfer fluid. These means can be means capable of causing a congealing of one of the two liquids.

The microfluidic device can further comprise at least second controlling means for controlling the progression of said liquid between the two liquids, placed down stream of the first controlling means and able to cause, when actuated, the stopping or the slowing of the progression of said liquid over the zone of each micro-channel by effecting an action based on a physico-chemical property of said liquid, said action not having a direct affect on the other liquid. The second controlling means can be chosen from the means operating thermally, means operating on a viscosity basis for slowing, means operating on the basis of magnetic effect, means operating on the basis of electrowetting and means operating by constriction of the tubes. The second controlling means operating thermally, the controlling means being chosen from the Peltier effect devices and thermal transfer fluid. These means can also be means capable of causing a congealing of one of the two liquids.

A further object of the invention is a biological reactor comprising first distributing means of the liquid for forming mobile reaction chambers;

second distributing means of liquid for forming non-miscible segmenters;

a microfluidic device such as defined above whose injection means are connected alternatingly to the first distributing means and to the second distributing means so as to provide, in the micro-channels of the microfluidic device, series of mobile reaction chambers with non-miscible segmenters;

a micro-system enabling realization of a biological procedure on the samples circulating in the channels of the micro-system, the micro-system comprising for each channel a first input opening connected to a corresponding micro-channel of the microfluidic device and a second input opening connected to corresponding sample injecting means in the reaction chambers.

Further still, the invention has the object of a method of implementing of a biological, biochemical, or chemical procedure upon the samples, comprising:

the formation in a microfluidic device such as the one described above of series of mobile reaction chambers with non-miscible segmenters in micro-channels, the series being formed in parallel and in a synchronized fashion;

simultaneous injection of series of mobile reaction chambers with non-miscible segmenters, formed in the micro-channels of the microfluidic device, into the channels of a micro-system in a number corresponding to that of the micro-channels of the microfluidic device;

simultaneous and parallel injection of samples into the channels of the micro-system so as to mix them in synchronized fashion with the mobile reaction chambers circulating in the channels of the micro-system;

realization of a biological, biochemical or chemical procedure on the samples having been mixed with the mobile reaction chambers.

BRIEF DESCRIPTION OF THE FIGURES

The invention will be better understood and other advantages more apparent on reading the following exemplary but non-limiting description together with the accompanying figures, wherein:

FIG. 1, already described, schematically represents a reaction series wherein several volumes of different reactions can be circulated;

FIGS. 2A to 2G are sectional views of a parallel and synchronized injecting device according to the invention and shown in use;

DETAILED DESCRIPTION OF THE EMBODIMENTS OF THE INVENTION

Figure 2B:
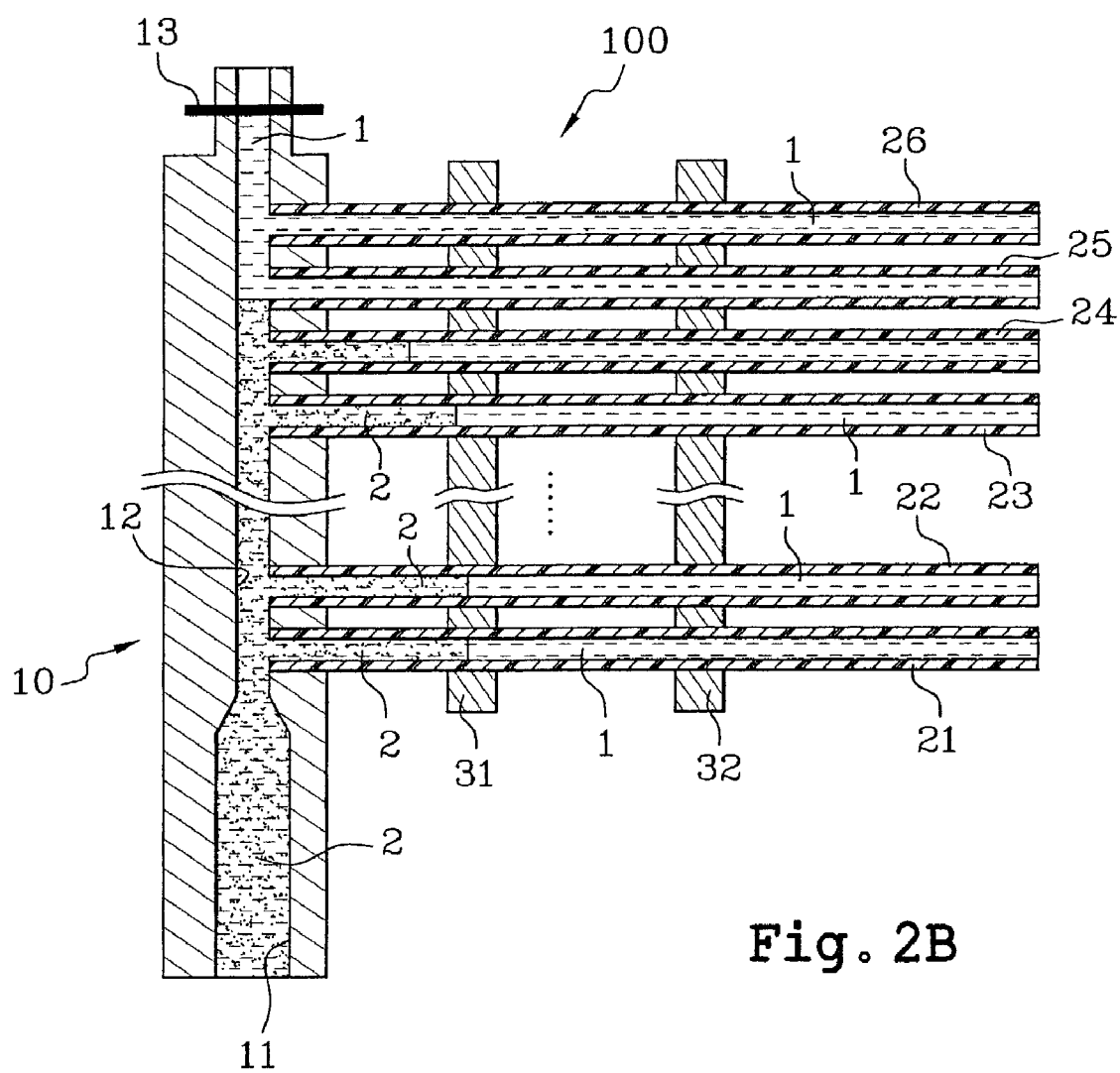

FIGS. 2A to 2G are sectional views of the parallel and synchronized injecting device according to the invention.

The injecting device is comprised of an elongated part 10 perforated along its longitudinal axis by a traversing hole forming an injection chamber and comprising a channel input 11 extended by an injection channel 12. The part 10 also comprises holes in the axis perpendicular to the axis of the injection channel 12 and leading into the injection channel 12. These holes are used for accommodating the first ends of micro-capillaries 21 to 26 or micro-channels. The micro-capillaries are formed, for example, using molten silicon and are lined with polyimide of the type described in international application WO-A-00/30751, for example.

They can be of very small diameter, typically several μm to several hundreds of μm. They can be fixed to the part 10 by gluing.

The second ends of the micro-capillaries can be formed by a micro-system (not shown).

The input 11 of the channel is connected to a tube from which the successive liquids that are to be circulated into the micro-channels are injected. A valve 13 is arranged at the end of the injection channel opposite to the input 11. The injections can be made using a pump, a plunger syringe or by a pressure difference between the upstream and downstream of the microfluidic circuit assembly.

The injecting device can be formed by using other techniques, in particular micro-machining techniques such as those utilized in WO-A-01/07159.

As shown in FIG. 2A, the micro-capillaries or microchannels 21 to 26 are arranged parallel to each other and on the same plane.

Two thermal elements are arranged perpendicularly to the micro-capillaries. They are consequently parallel to the injection channel 12 and define the thermal zones 31 and 32. The thermal zones can be formed using Peltier effect resistances. They can also be formed by using a thermo-transferring fluid (liquid or gas), circulating in proximity to the micro-capillaries. It is therefore advantageous to select a design that enables locating the thermal zone along the micro-capillaries. For example, a part formed of a material having good thermal conducting properties such as brass, copper or aluminum and having holes, through which the micro-capillaries are passed, could be used. Said part is glued to a Peltier effect device. Said configuration allows limiting the thermal zone by assuring good thermal contact.

The function of the device according to the invention will now be described with reference to FIGS. 2A to 2G, the device providing series of mobile reaction chambers and segmenters in micro-capillaries. It is assumed that the reaction chambers are constructed using an aqueous solution that is in the frozen state at a temperature $T_1$ of −20° C. and in the liquid state at ambient temperature $T_2$. The segmenters are formed using oil that is in the liquid state at temperatures $T_1$ and $T_2$.

As shown in FIG. 2A, the valve 13 is closed and the entire device assembly is filled with oil 1. The thermal zone 31 is then brought to temperature $T_1$.

As shown in FIG. 2B, an aqueous reaction solution 2 is introduced into the injection channel 12 and begins to fill the microcapillaries 21 to 26 at the rate of its progression in the injection channel 12. When the solution 2 reaches the level of the thermal zone 31 the progression of this solution in the particular micro-capillary stops by reason of the congealing of the solution in that zone. In this way, the parts of the micro-capillaries between their ends situated in the part 10 and the thermal zone 31 are all filled with the same volume of solution 2 if the micro-capillaries are of the identical cross-section.

Figure 2C:
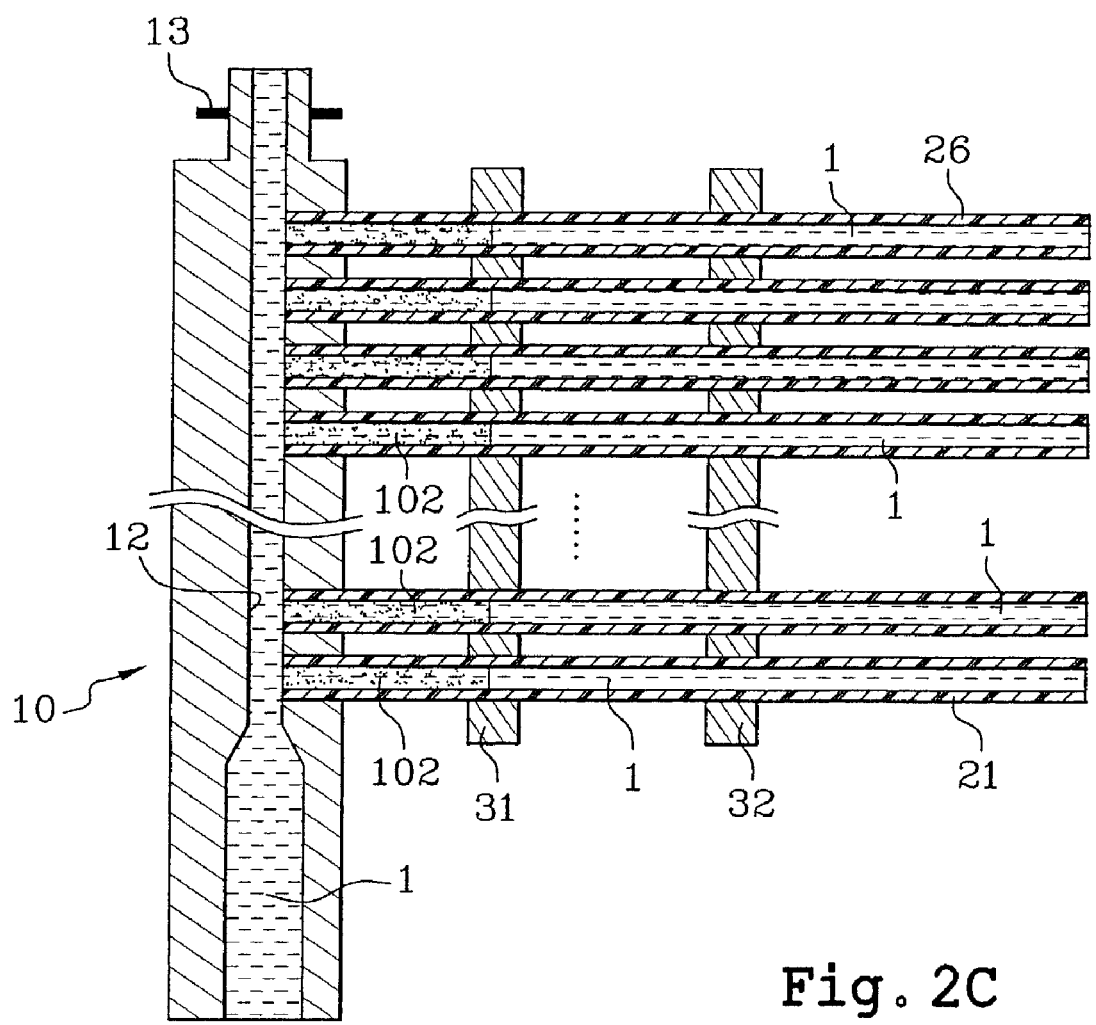

The valve 13 is then opened and allows purging of the injection channel 12 and refilling with the liquid intended to form the segmenting beads; that is, the oil 1. This is shown in FIG. 2C. The first reaction chambers 102 are thus formed.

The valve 13 is then closed. The temperature of the thermal zone 31 goes from $T_1$ to $T_2$ the effect of which is the congealing of the aqueous solution in the zone 31 and enabling circulation of the liquids in the micro-capillaries 21 to 26.

Figure 2D:
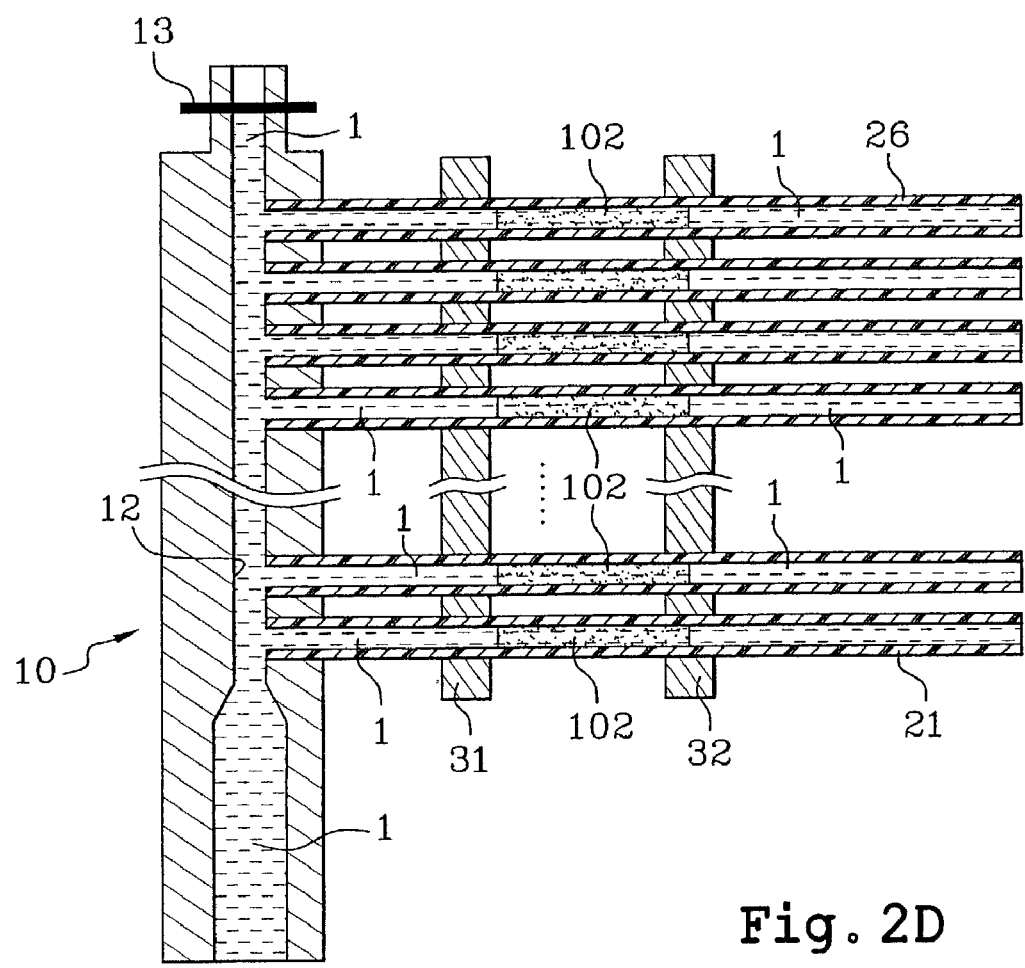
Figure 2E:
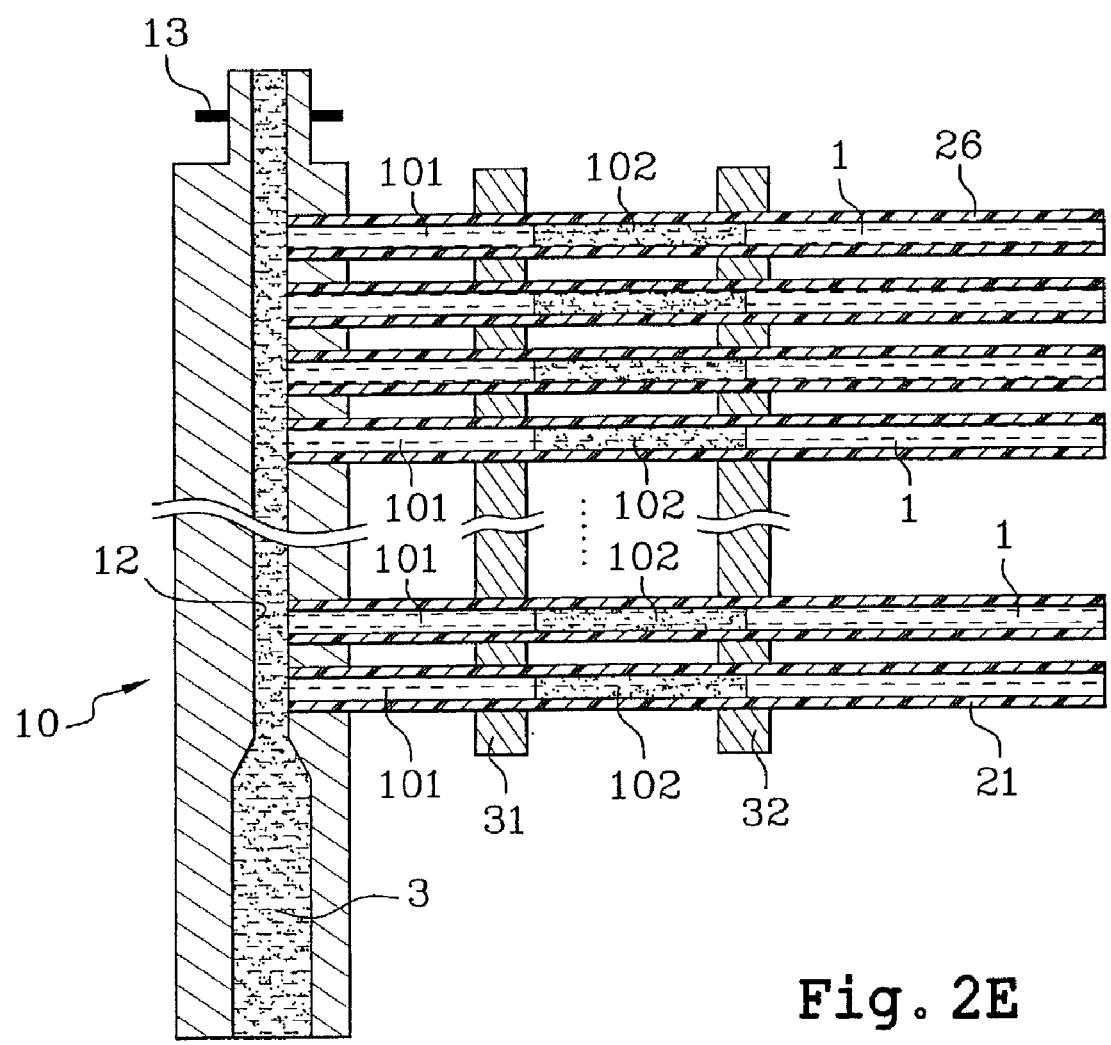

The thermal zone 32 passes from temperature $T_2$ to $T_1$. The oil 1 continues to be injected which causes the movement of the reaction chambers 102 previously formed towards the thermal zone 32. The reaction chambers 102 stop in parallel when they abut the thermal zone 32, the aqueous solution freezing at this level. This is shown in FIG. 2D.

The valve 13 is then opened anew. The injection channel 12 is purged and filled with an aqueous reaction solution 3 which can be different from the previous aqueous reaction solution (see FIG. 2E). In this fashion a segmenting bead 101 is formed in each micro-capillary following the mobile reaction chamber previously formed. Each segmenting bead 101 has the same length.

The valve 13 is then closed. The thermal zone 32 passes from $T_1$ to $T_2$ temperature which enables circulation of the liquids in the micro-capillaries 21 to 26 while injection of the aqueous solution 3 continues into the injection channel 12 (see FIG. 2F).

Figure 2F:
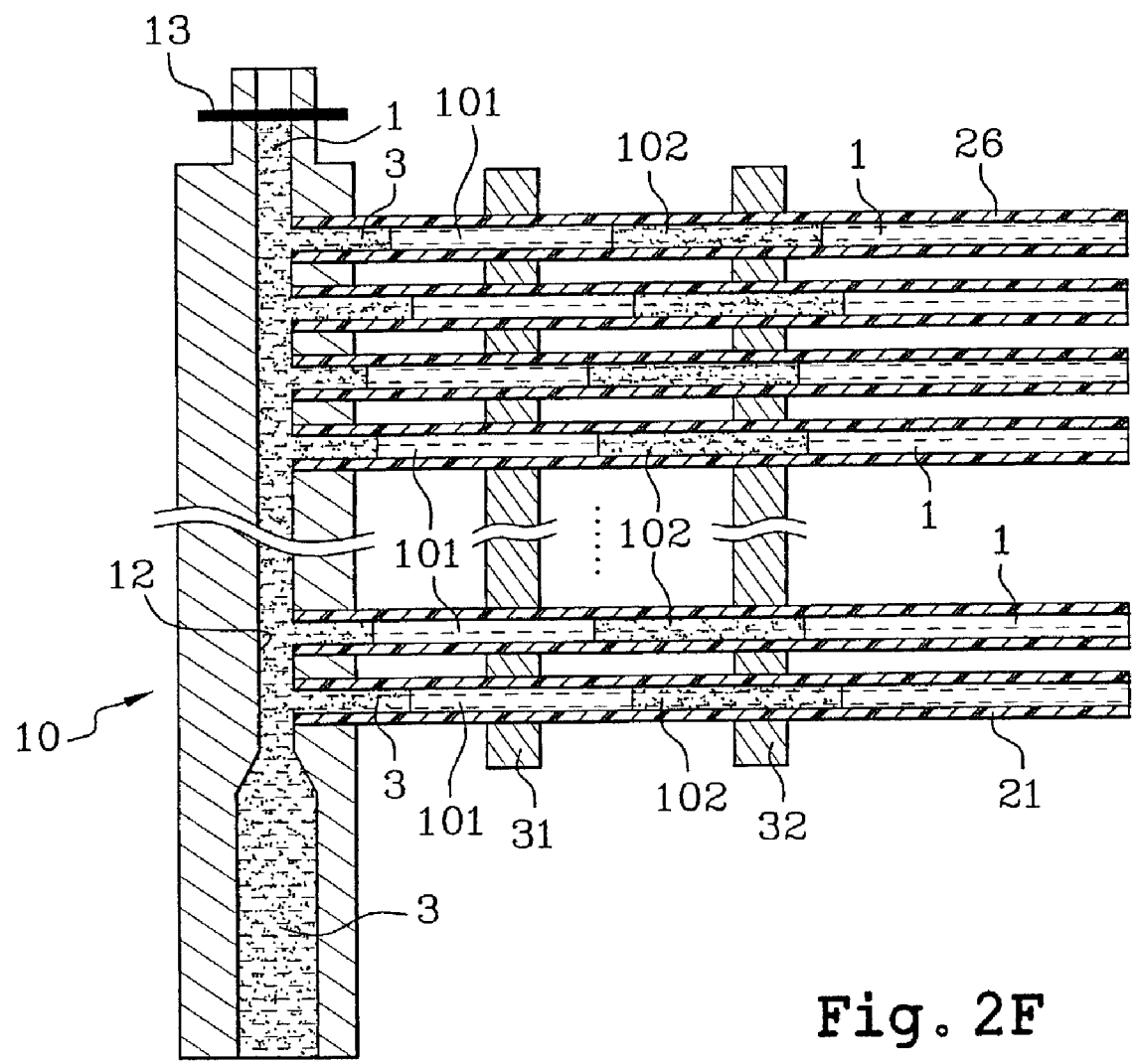
Figure 2G:
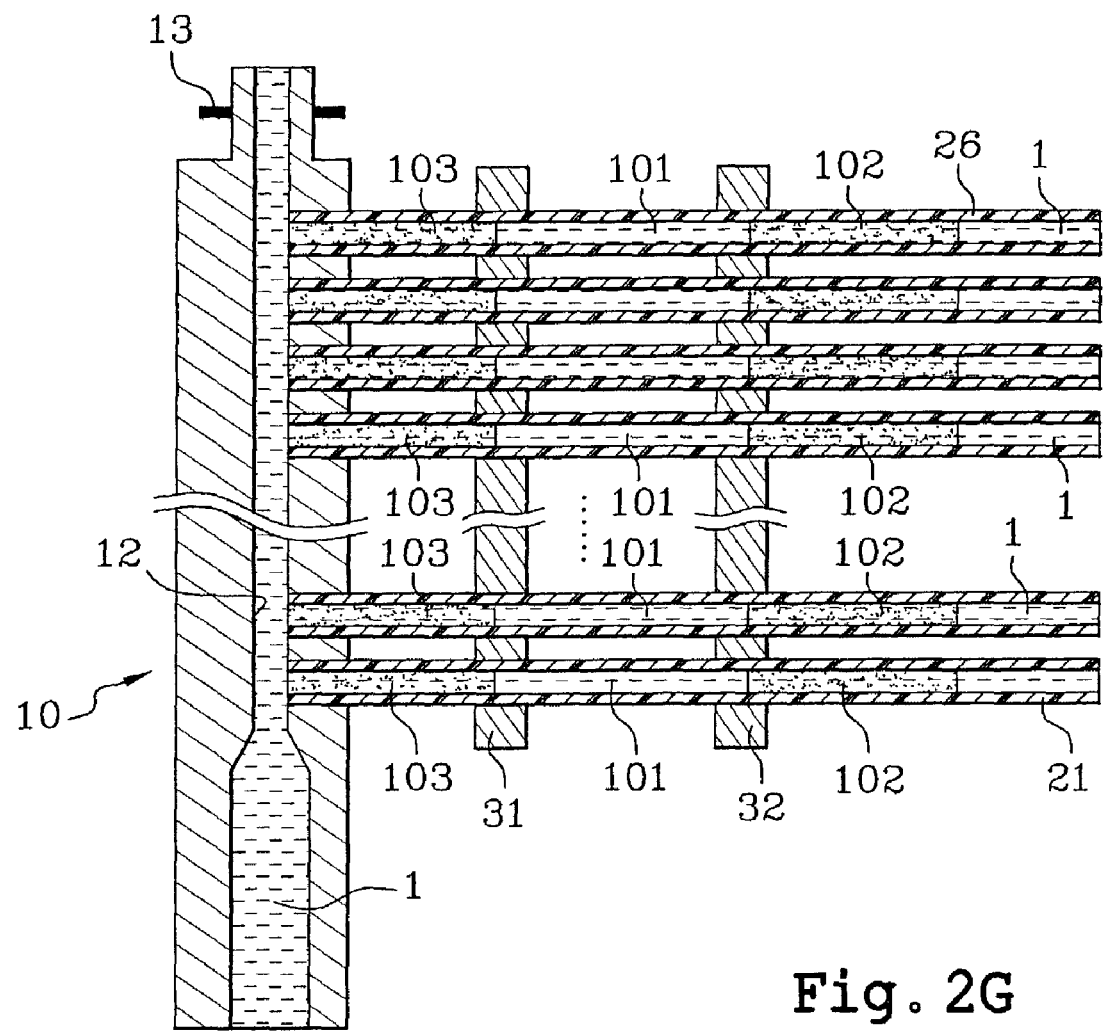

The thermal zone 31 is brought to temperature $T_1$ which causes the stopping of the aqueous solution 3 in process of injection into the micro-capillaries 21 to 26 when said aqueous solution 3 reaches the level of the thermal zone 31. The valve 13 is then opened. The injection channel 12 is purged and is again filled with oil 1, as shown in FIG. 2G. The second reaction chambers 103 are so formed.

The cycle of creating the segmenting beads and the reaction chambers can then be resumed after having passed the thermal zone 31 at temperature $T_2$.

In certain cases one or several constituents of the reaction chambers can be sensitive to the low temperatures or to freezing. For example, certain biological reactions involve the use of enzymes whose activity is annihilated when they are in a frozen aqueous solution. In such cases the constituent that is sensitive to the temperature can be added to the reaction chamber after it has left the second thermal zone 32, preventing the situation wherein the sensitive constituent from being subjected the freezing $T_1$ temperature. The temperature-sensitive constituents can then be introduced into the reaction chambers by a number of possible routes; for example, by using a plurality of lateral channels connected to the micro-capillaries 21 to 26 arranged distally relative to the thermal zone 32 and sampling the sensitive constituent at the temperature in a particular reservoir.

During certain phases, the flows can become slightly desynchronized. This is shown in FIG. 2F where there is a shift between the reaction chambers 102 already formed. In effect, it can be difficult to assure a uniform flow/pressure relation over all of the micro-capillaries. In particular, with the flows comprising interfaces between the non-miscible liquids, it has been shown that the flow/pressure correlation is complex. In fact, it is necessary to take into account the capillarity forces resulting from menisci between the two surfaces. Controlling the phenomena of wetting/dewetting in the channels is generally quite complex and can create a desynchronization problem from one channel to another. Therefore, the mode of injecting according to this invention allows resynchronizing of the flows for each injection. The exemplary embodiment represented in FIGS. 2A to 2G comprises two intervention zones, zones 31 and 32, but other zones can be provided so as to better control the advance of the reaction series and limiting desynchronization.

The means for controlling the progression of one of the two liquids in the micro-channels can be applied to one or the other of the liquids to be circulated. Controlling means other than the thermal means can be used to arrest or to decelerate the progression of the liquids. A slowing method using viscosity, a method using magnetic effect, an electrowetting method and a tube constriction method can be mentioned.

The slowing method using viscosity can be used by the same architecture as that shown in FIGS. 2A to 2G. However, the temperature acts on a viscosity difference between the two phases, this difference necessarily being more significant when the controlling means are active.

Figure 3:
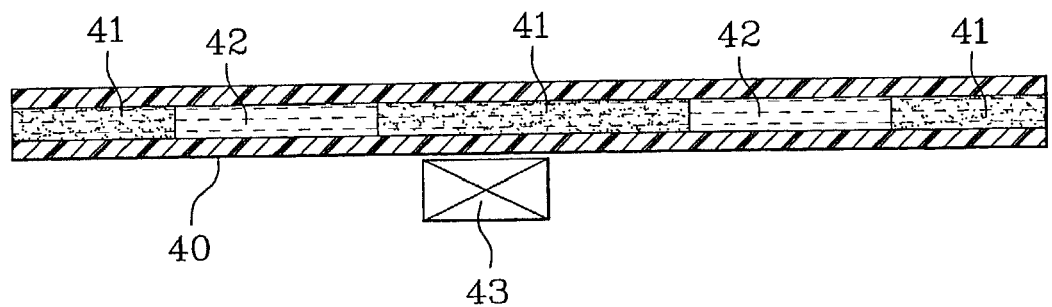
FIG. 3 represents a detail view of a microchannel of a parallel and synchronized injecting device according to the invention using magnetic controlling means.

To illustrate the method based on magnetic effect only one portion of a single micro-channel or micro-capillary 40 has been shown in longitudinal section in FIG. 3, it being understood that the magnetic effect method applies to any micro-channel for obtaining a parallel synchronized injection. The one of the two liquids 41 and 42, the liquid 42 for example, contains ferro-magnetic particles that are sensitive to a magnetic field. It is therefore a ferro-fluid or a magnetic fluid. The other liquid does not contain ferro-magnetic particles. The magnets or the electromagnets 43 can then be used in lieu of the thermal zones of the device shown in FIGS. 2A to 2G to assure the same functions.

Mageneto-rheological fluids can also be used, whose viscosity can be increased by a factor of 1000 under the effects of a magnetic field (see the U.S. Pat. No. 5,549,837).

The controlling means of the progression of one of the two liquids can be produced by electrowetting effect. By electrowetting or electrocapillarity the property of modification of the surface energy between one liquid and the wall is determined by the application of an electrostatic field. Reference on this subject can be made to the document, "*Electrocapillarity and wetting of insulating films by water.*" by Gruno BERGE, C. R. Acad. Sci. Paris. Vol. 317, No. II, pages 157–163, 1993 or to the document "*Surface tension driven microactuation based on continuous electrowetting (CEW)*" by Junghoon LEE and Chang-jin KIM, Journal of Microelectromechanical Systems, Vol. 9, No. 2, pages 171–180, 2000. This property depends on the nature of the liquids (conductivity, permeability, etc.). Thus, it is possible to act selectively on one of the two liquids circulating in the device. It is thus sufficient to replace the thermal element used n the device illustrated by FIGS. 2A to 2G by a set of electrodes that enable the creation of an electrostatic field in the micro-capillaries.

Figure 4:
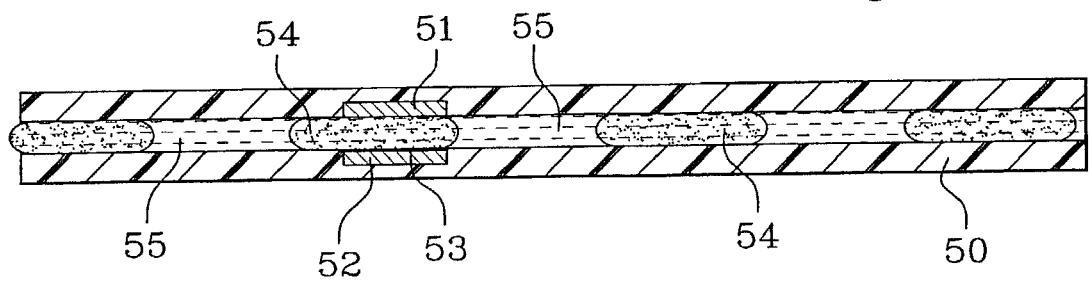
FIG. 4 represents a detail view of a microchannel of a parallel and synchronized injecting device according to the invention using electrowetting controlling means.

To illustrate the method by electrowetting effect, only a portion of a single micro-capillary 50 has been represented in FIG. 4 in longitudinal section, it being understood that this mode applies to all micro-capillaries used for obtaining parallel and synchronized injection. The micro-capillary 50 comprises two electrodes 51 and 52 placed, respectively, on the upper wall and on the lower wall of the micro-capillary 50. In this example, a passivation layer 53 is deposited on the lower electrode 52, the inner side facing the micro-capillary. This passivation layer can be deposited on the other electrode 51 or even on each of the electrodes 51 and 52. The micro-capillary 50 moves a series of mobile reaction chambers 54, comprised of an aqueous solution, and isolation beads 55 comprised of an insulation liquid, oil for example. The dielectric properties of the liquids comprising the mobile chambers 54 and the isolation beads 55 are different. When a difference in potential is applied between the electrodes 51 and 52 and comprising a reaction chamber 54 is present between the electrodes 51 and 52, it is observed that the wettability of this liquid to the wall is increased. It is thus possible to modify the fluid behavior of the micro-capillary. In particular, it is possible to stop the flow when the liquid from one mobile chamber 54 is present at electrodes 51 and 52. When the difference in potential between these electrodes is suppressed, circulation of the liquids can resume.

Figure 5:
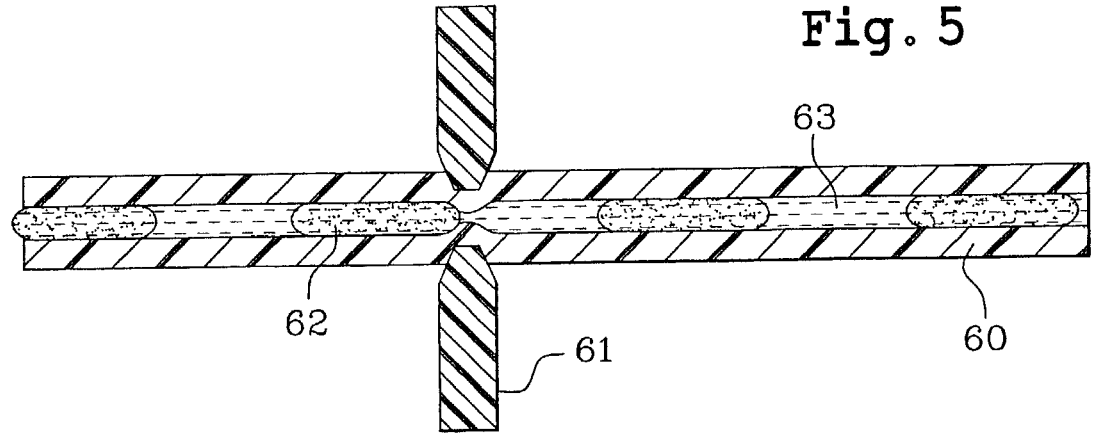
FIG. 5 represents a detail view of a microchannel of a parallel and synchronized injecting device according to the invention using tube-constriction controlling means.

To illustrate the method by tube constriction, only a portion of a single micro-capillary 60 has been represented in FIG. 5 in longitudinal section, it being understood that this mode applies to all micro-capillaries used for obtaining parallel and synchronized injection. The capillary 60 has at least one deformable part. That part is, for example, made of polymer or silicone. Constriction of said part can be effected by a mechanical system represented at reference 61.

It is well-known that that the capillary pressure resulting from a meniscus in the capillary depends on the cross-section of the capillary. This property is used for immobilizing the menisci. It is sufficient, for example, to have an abrupt section variation in the capillary. This has already found a number of applications. On this subject reference is made to the document, "Design analysis of capillary burst valves in centrifugal microfluids," of Jun ZENG et al., appearing in *Micro Total Analysis Systems,* 2000, Kluwer Academic Publishers, pages 579–582. This property can be used in the context of the present invention by replacing the thermal zones of the device shown in FIGS. 2A to 2G by a constriction of the capillaries inducing an abrupt section variation in the micro-channel.

Preferably, the interior of the micro-channel or micro-capillary 60 is hydrophobic, the mobile reaction chambers 62 are formed of an aqueous phase and the segmenting beads 63 are formed of a phase that is not miscible with the aqueous phase, oil for example. Thus it is possible to stop the flow when a new mobile reaction chamber reaches the level of the constriction. Releasing the constriction makes possible the circulation of the reaction series.

Figure 6:
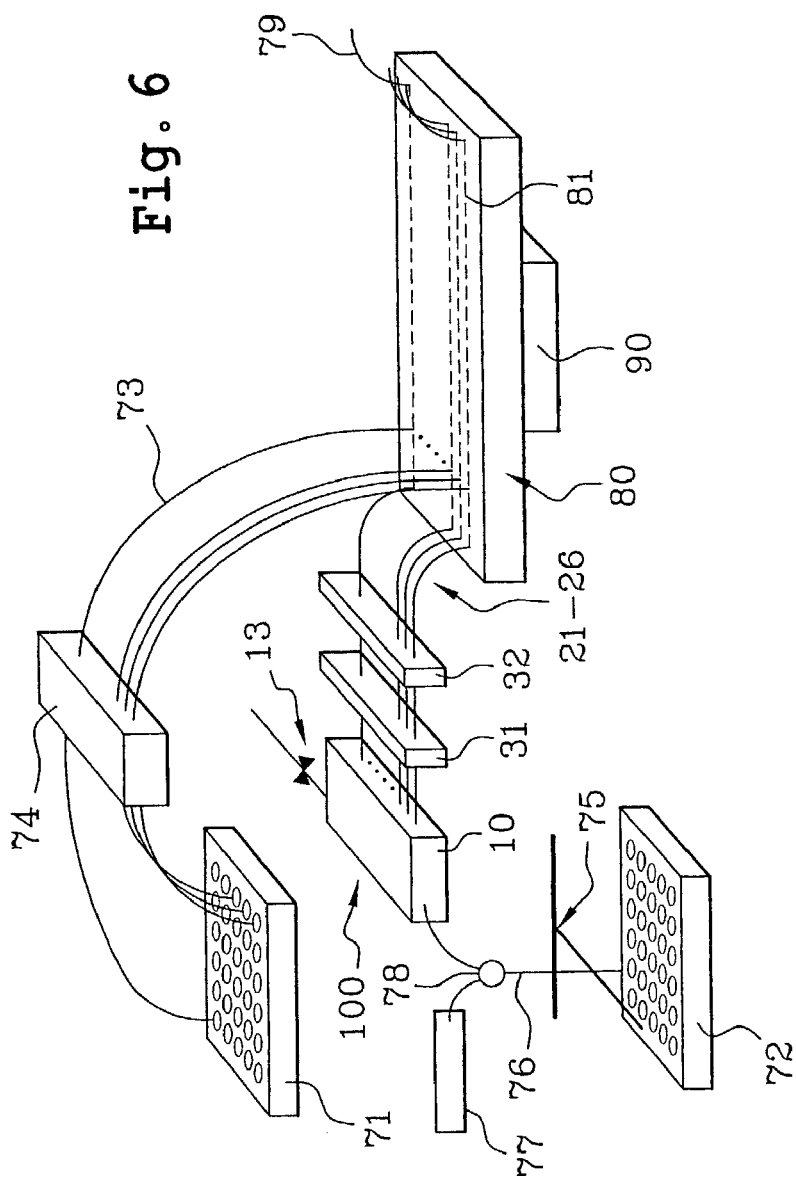
FIG. 6 schematically represents a biological reactor using the parallel and synchronized injecting device according to the invention.

FIG. 6 represents a biological reactor using the parallel synchronized injecting device 100 according to the invention, whose function is represented by FIGS. 2A to 2G.

FIG. 6 shows a well plate 71 containing N samples to be assayed and a well plate 72 containing M different reactants. An assay corresponds to a mixing of one reactant and one sample according to a biological procedure. The biological procedure is done in a microfluidic component or micro-system 80 comprised of channels 81. The component 80 is shown in longitudinal section in FIG. 7. The number of channels 81 is preferably equal to N.

The biological reactor of FIG. 6 enables N×M reactions to be carried out in continuous flow.

Each channel 81 is connected to one of the wells of the well plate 71 by micro-tubes 73. Thus, the same sample circulates continuously in the same channel. This implementation provides the advantage of eliminating any risk of contamination between two different samples. Injection of the samples can be done by using a pump 74, for example a peristaltic pump.

Reference 75 identifies a schematic robot that enables moving a needle or a pipette 76 into each well of the well plate 72 containing the M reactants. Aspiration of the reactants and injecting them into the micro-system 80 are assured by a plunger syringe 77 and a distribution valve 78. The robot 75 also enables sending the needle 76 to a container (not shown) containing the liquid that is non-miscible with the reactants and necessary to forming the reaction series.

References 10, 13, 31, 32, and 21 to 26 identify the same elements as those represented in FIG. 2A. The micro-capillaries of the device 100 certainly of of the a number equivalent to the number of channels 81. References 31 and 32 designate the thermal zones, for example.

Figure 7:
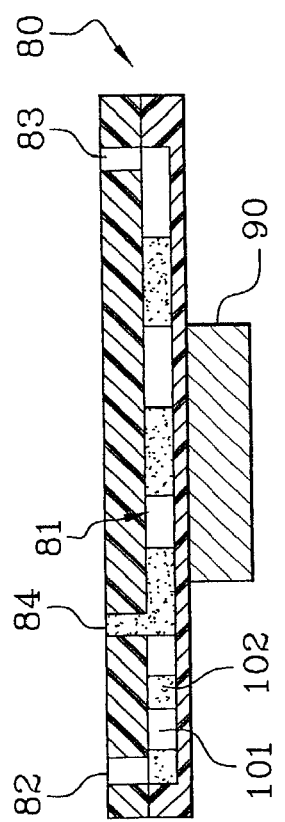
FIG. 7 represents an axial section of a microfluidic component used in the biological reactor represented in FIG. 6.

FIG. 7 shows the micro-system 80 obtained by adhering two superpositioned plates. The section was made along the axis of one channel 81 that has an input opening 82 and an output opening 83.

The capillaries 21–26 are connected to the component 80 by the input openings 82. According to the procedure used, the reaction products are evacuated to a waste receptacle, to a detector or to another micro-system through the outlet openings 83 connected to the capillaries 79.

The micro-system 80 further comprises openings 84 leading to the channels 81. These openings 84 receive the micro-tubes 73. An element 90 is mounted under the micro-system 80. It is, for example, a Peltier effect devices that allows producing of temperature cycles for the liquids circulating in the channels 81.

The injecting device according to the invention enables generation of reaction series comprising mobile reaction chambers 102 and segmenting beats 101 over N capillaries in parallel and synchronized. The reaction series reach the channels 81 of the micro-system 80. The mobile reaction chambers are then mixed with the reactants sent through the openings 84 through the micro-tubes 73 to produce the reaction products 110. The configuration utilized thus enables performing the different N×M reactions in continuous flow.

The devices and the procedure according to the invention can be used for performing a large variety of biological, biochemical, and chemical procedures, including amplification reactions (PCR or LCR, for example), genotype assays (micro-sequencing, for example), procedures for structural characterization of complex polysaccharides, chemical synthetic procedures, etc.

By way of example, it is possible by using this biological reactor to perform a DNA amplification reaction, in particular a PCR (i.e., polymerase chain reaction). In this context reference can be made to WO-A-01/07159, which discloses a micro-system of the type referred to at 80 in FIGS. 6 and 7 and a method of performing the PCR procedure in continuous flow in rectilinear channels traversing zones of variable temperature. The number of reactions obtained, for example, of 96×96 when using plates with 96 wells for the DNA samples and the PCR reagents.

The invention provides a number of advantages with respect to the prior art. The reaction series can be comprised of different reagents. Injecting is done in parallel over a plurality of capillaries using volumes that can be less than μl, the volumes being injected with a precision of at least 0.01 μl. It can be enhanced by appropriate dimensioning of the capillaries and the reaction zones. Control is common to all capillaries. The dead volumes are very small. In fact, the dead volume across the entire set of capillaries is of the order of the volume of the injection channel 12. The reaction series injected can comprise an unlimited number of reagents (200 or more, for example). The system according to the invention is simple to use: no feedback, no complex technology. Dimensions of the system (distance between the injection channel 12 and the zones 31, 32) enable automatic calibration of the mobile reaction chamber volumes and the segmenting beads. The flows over all of the capillaries remains calibrated. It is possible to use a plurality of modes of operation, which allows selection of the optimal mode compatible with the intended application. Injection is compatible with stocking of the reagents in any type of well plate used in biology.

The invention claimed is:

1. A microfluidic device, comprising:
   plural micro-channels;
   means for injecting plural liquids including a first liquid and a second liquid alternately into each of the plural micro-channels, the first liquid being provided to form mobile reaction chambers and the second liquid being provided to form non-miscible segmenters in each of the plural micro-channels; and
   means for controlling a progression of one of the plural liquids in the plural micro-channels by forming at least one zone in each of the plural micro-channels to effect, when activated, at least one action on the at least one zone so as to delimit an injection volume of said one of the plural liquids in each of the plural micro-channels, the at least one action being based on a physico-chemical property of said one of the plural liquids, and not directly affecting another of the plural liquids.

2. A microfluidic device according to claim 1, wherein said means for controlling enables movements of said at least one zone of each of the plural micro-channels in order to modify the injection volume of said one of the plural liquids.

3. A microfluidic device according to claim 1, wherein the plural micro-channels each have first ends, and the means for injecting comprises a part having an injection channel communicating with the first ends of the plural micro-channels.

4. A microfluidic device according to claim 3, wherein the injection channel has two ends, one of the two ends communicating with a channel input through which the plural liquids are injected, another of the two ends being equipped with means for evacuating the plural liquids present in the injection channel.

5. A microfluidic device according to claim 4, wherein the means for evacuating comprises a valve.

6. A microfluidic device according to claim 1, wherein the means for controlling is selected from means for operating thermally, means for operating by electrowetting and means for operating by mechanical tube constriction.

7. A microfluidic device according to claim 6, wherein the means for operating thermally is selected from devices using a Peltier effect and thermal-transfer devices.

8. A microfluidic device according to claim 7, wherein the means for operating thermally is capable of one of inducing congealing of one of the plural liquids and slowing one of the plural liquids by acting on viscosity characteristics of the one of the plural liquids.

9. A microfluidic device according to claim 3, wherein the injection channel and said at least one zone of each of the plural micro-channels are arranged in parallel, the plural micro-channels being perpendicular to the injection channel.

10. A microfluidic device according to claim 1, wherein the means for controlling comprises at least two controlling devices configured to control the progression of said one of the plural liquids in the plural micro-channels, by forming at least two zones in each of the plural micro-channels to effect, when activated, actions on the at least two zones, the actions being based on a physico-chemical property of said one of the plural liquids, said action not directly affecting the another of the plural liquids.

11. A microfluidic device according to claim 10, wherein each of the at least two controlling devices is selected from among a device configured to operate thermally, a device configured to operate by electrowetting and a device configured to operate by mechanical tube constriction.

12. A microfluidic device according to claim 11, wherein the device configured to operate thermally is selected from devices using a Peltier effect and thermal-transfer devices.

13. A microfluidic device according to claim 12, wherein the device configured to operate thermally is capable of one of inducing congealing of one of the plural liquids and slowing one of the plural liquids by acting on viscosity characteristics of the one of the plural liquids.

14. A biological reactor comprising:
the microfluidic device according to claim 1;
means for distributing connected to the means for injecting the plural liquids wherein the first liquid and the second liquid are provided by the means for distributing to the means for injecting the plural liquids, and injected by the means for injecting the plural liquids into the plural micro-channels of the microfluidic device alternately in series; and
a micro-system comprising:
means for injecting samples;
plural channels each of which having a first input opening connected to a corresponding one of the plural micro-channels of the microfluidic device and a second input opening connected to the means for injecting samples which injects the samples into the mobile reaction chambers in the plural channels.

15. A microfluidic device comprising:
plural micro-channels;
an injecting device configured to alternately inject plural liquids into each of the plural micro-channels; and
at least one controlling device positioned to form at least one zone in each of the plural micro-channels and configured to control a progression of one of the plural liquids flowing through the plural micro-channels by effecting at least one action on the at least one zone based on a physico-chemical property of the one of the plural liquids, the action not directly affecting another of the plural liquids.

16. A microfluidic device according to claim 15, wherein the at least one controlling device is selected from a device configured to operate thermally, a device configured to operate on a basis of viscosity, a device configured to operate on a basis of a magnetic effect, a device configured to operate by electrowetting and a device configured to operate by tube constriction.

17. A microfluidic device according to claim 16, wherein the device configured to operate thermally is selected from devices using a Peltier effect and thermal-transfer devices.

18. A microfluidic device according to claim 17, wherein the device configured to operate thermally is capable of inducing congealing of one of the plural liquids.

19. A micro-reactor comprising:
the microfluidic device according to claim 15;
at least one distributing device configured to distribute the plural liquids, wherein the injecting device is connected to the at least one distributing device so as to provide the plural liquids alternately in series into the plural micro-channels of the microfluidic device; and
a micro-system comprising:
a sample injecting device configured to inject samples;
plural channels each of which having a first input opening connected to a corresponding one of the plural micro-channels of the microfluidic device and a second input opening connected to the sample injecting device which injects the samples into at least one of the plural liquids in the plural channels.

20. A microfluidic device, comprising:
plural micro-channels;
means for injecting plural liquids including a first liquid and a second liquid alternately into each of the plural micro-channels, the first liquid being provided to form mobile reaction chambers and the second liquid being provided to form non-miscible segmenters in each of the plural micro-channels; and
means for controlling a progression of one of the plural liquids in the plural micro-channels by forming at least one zone in each of the plural micro-channels to effect, when activated, at least one action on the at least one zone so as to delimit an injection volume of said one of the plural liquids in each of the plural micro-channels, the at least one action being based on a magnetic effect to a property of said one of the plural liquids, and not directly affecting another of the plural liquids.

* * * * *